Nov. 12, 1974
G. DE RUITER
ROSE PLANT
Filed May 31, 1973
Plant Pat. 3,648
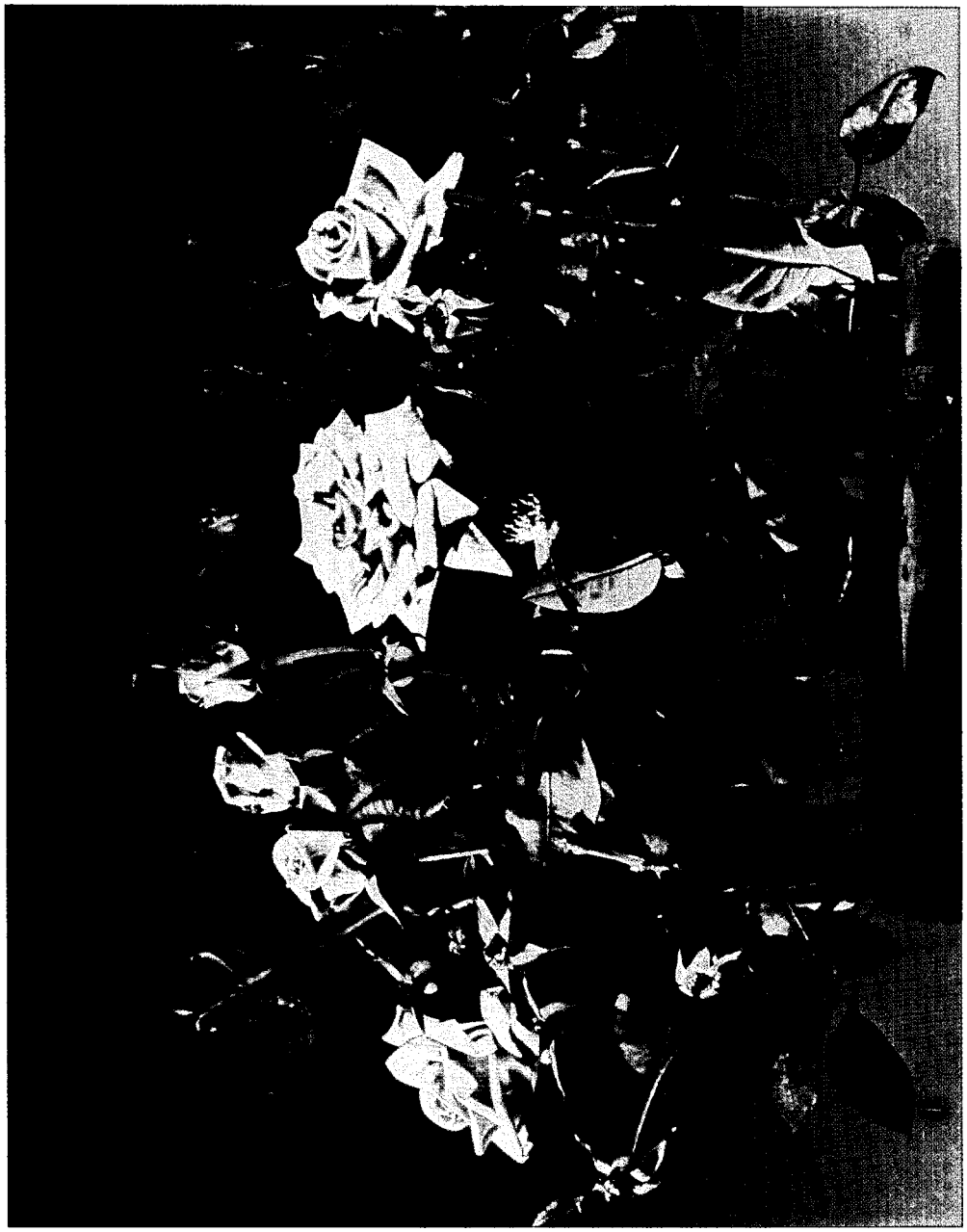

United States Patent Office

Plant Pat. 3,648
Patented Nov. 12, 1974

3,648

ROSE PLANT

Gijsbert de Ruiter, Hazerswoude, Netherlands, assignor to The Conrad-Pyle Company, West Grove, Pa.

Filed May 31, 1973, Ser. No. 365,441
Int. Cl. A01h 5/00
U.S. Cl. Plt.—17 1 Claim

ABSTRACT OF THE DISCLOSURE

A new and distinct variety of rose plant of the Hybrid Tea class, which was originated by crossing the variety Mischief (unpatented) with an unnamed seedling whose parentage was Queen Elizabeth (Plant Patent No. 1,259) crossed with Scania (unpatented).

SUMMARY OF THE INVENTION

The present invention relates to a new and distinct variety of rose plant of the Hybrid Tea class which was originated by me by crossing the variety Mischief (unpatented) with an unnamed seedling whose parentage was Queen Elizabeth (Plant Patent No. 1,259) × Scania (unpatented).

My objective in this breeding and in making these crosses was to produce a new and improved rose variety of superior winter-hardiness, vigorous growth, free flowering, combined with a distinctive color different from all other varieties. I was successful in my objective as evidenced by the following combination of characteristics which are outstanding in my new rose plant:

1. A plant of unusual vigor, freely branched and upright growth.
2. A plant habit with exceptional even, regular form and neat, attractive appearance.
3. A floriferous plant producing quantities of flowers usually one to a stem.
4. An attractive flower bud opening to a high-centered bloom, fully double with petals arranged regularly and loosely rolled outward.
5. Attractive and distinctive color best described as salmon-orange.
6. Foliage of attractive size, dark green color and covering the plant exceptionally well and having above average resistance to common garden diseases.
7. A plant of superior winter-hardiness and vigorous summer growth. Only very slight tip injury occurred at West Grove, Pennsylvania, in the winter of 1971–1972 when other varieties growing in the same location were injured and severely damaged by winter cold.

In comparison to its seed parent, my new rose is more vigorous in growth, has flowers of fewer petals and with more orange color in the flower.

The pollen parent of my new rose was an undisseminated seedling of Queen Elizabeth crossed with Scania, similar to Queen Elizabeth in growth habit but less vigorous and with orange-salmon flower color. My new rose is distinctive from its pollen parent by being more vigorous in growth, producing more flowers of a more attractive salmon-orange color and with more foliage.

Asexual reproduction of the new variety by budding as performed at Hazerswoude, Holland, and West Grove, Pennsylvania, United States of America, showed the characteristics and distinction come true to form and are established and transmitted through succeeding propagations.

BRIEF DESCRIPTION OF DRAWING

The accompanying drawing shows typical specimens of the vegetative growth and flowers of my new variety in different stages of development as depicted in color as nearly true as it is reasonably possible to make the same in a color illustration of this character.

DETAILED DESCRIPTION OF DISCLOSURE

The following is a detailed description of the new variety with color terminology in accordance with the Royal Horticultural Society Color Chart:

Type: Hardy; tall bush, outdoor; seedling; for garden decoration.
Class: Hybrid Tea.
Propagation: It does hold its distinguishing characteristics through succeeding propagations by budding.

FLOWER

Locality Where Grown: West Grove, Pennsylvania.
Flowers Borne: Singly and several to stem; on normal medium long stems.
Quantity of Bloom: Free outdoors.
Continuity: Continuous.
Fragrance: Moderate; fruity.
Bud: Peduncle: Medium long; medium slender; bending; reddish 46A; medium rough; medium number; prickles; red.

*Before calyx breaks.*—Size: Medium small. Form: Ovoid with a conspicuous neck; without foliaceous appendages on the surface of the bud; with slender foliaceous parts extending beyond the tip of the bud equal to ¾ or more of its length.

*As calyx breaks.*—Color: 46C, shaded with 53A.

*As first petal opens.*—Size: Medium small. Form: Medium length; pointed. Color: Outside: 46B. Inside: 41A.

*Opening.*—It does open up well.

Bloom: Size when fully open: Medium, 3½ to 4 inches.

*Petalage.*—Double (usually with stamens showing); from 25 to 30 petals; arranged regularly.

*Form.*—High centered at first; becoming open; petals remaining at first tightly rolled outward; becoming later at maturity loosely rolled outward.

Petals: Medium leathery; with inside velvety; outside satiny.

*Shape.*—Outer: Obovate; with 1 notch; top edges rolled back forming a point. Intermediate: Obovate; with 1 tooth. Inner: Obovate; with 1 notch.

This description of a newly opened flower was made from a rose grown outdoors in September, 1972, at West Grove, Pennsylvania.

*Color.*—Outer petal: Outside surface—47C, blending to 48C near the base of the petal; Inside surface—43B, with greater saturation of the color upon increased light intensity. Intermediate petal: Outside surface—52C; Inside surface: 44C, with greater color saturation in sunlight and bright overcast sky. Inner petal: Outside surface—52C; Inside surface—40A.

This description was made from a rose that was open for three days outdoors in September, 1972, at West Grove, Pennsylvania.

*Color.*—Outer petal: Outside surface—52B; Inside surface—43C at petal margin, blending to 43D near petal base; 41B, lower part of petal; 11D, base of petal. Inner petal: Outside surface—52B; Inside surface—43C, with greater color saturation in bright overcast or sunlight; 41B, lower part of petal; 11D, at point of attachment.

General color effect:

*Newly opened flower.*—41B, with greater color saturation in bright overcast or sunlight.

*Three days open.*—Between 41B and 41C.

Behavior: Drop off cleanly; petals of heavy texture and substance are less affected by cold, wet weather and hot dry weather than most other varieties characteristic of the class.

Flower longevity: On bush 3 days in August and September, grown outdoors, kept at living room temperatures 4 days in September.

REPRODUCTIVE ORGANS

Stamens: Medium; arranged regularly about pistils.
Filaments: Most with anthers; long. Color: 39B.
Anthers: Medium size. Color: 34B. Seldom an anther fused with a petaloid.
Pollen: Moderate; yellow.
Pistils: Medium number.
Styles: Uneven; medium length; thin, bunched, columnar.
Stigma: White 11D.
Ovaries: Some protruding from receptacle.
Hips: Short, globular with inconspicuous neck; moderately smooth; walls thick, fleshy; green.
Sepals: Permanent; medium long; straight, spear shaped.
Seeds: Medium amount; medium size.

PLANT

Foliage: Leaves: Compound of 3, 5 leaflets; abundant; medium large; leathery, glossy.

*Leaflets.*—Shape: Pinnate with apex acute, base acute, serrate.

*Color.*—Mature—Upper surface: 137A; Under surface: 138B. Young—Upper surface: 187B; Under surface: 187C.

*Rachis.*—Medium. Upper side: Smooth, grooved. Under side: Sparsely thorny.

*Stipules.*—Medium length; medium wide; with short medium points; turning out at an angle of more than 45°; recurved toward the stem.

*Disease.*—Resistance superior to the average variety growing under the same cultural conditions.

Growth:

*Habit.*—Upright, much branched.
*Growth.*—Vigorous.
*Canes.*—Medium heavy.
*Main stems.*—Dull. Color: 137B.
*Prickles.*—Few. Color: 165C.
*Hairs.*—None.
*Branches.*—Dull. Color: 137B.
*Prickles.*—Few. Color: 165C.
*Hairs.*—None.
*New Shoots.*—Dull. Color: 187B. 145B just above axillary bud shading to 187B opposite next axillary bud above.
*Prickles.*—Several. Color: 187A.
*Hairs.*—None.

I claim:

1. A new and distinct variety of rose plant of the Hybrid Tea class substantially as herein shown and described, characterized particularly as to novelty by the unique combination of a vigorous, upright plant of even, balanced, attractive growth habit, covered with dark green glossy foliage in abundance and with flowers borne freely, usually one to a stem, with few prickles, and having an urn shaped bud of attractive salmon-orange color opening to a fully double flower of high center, medium size of the same salmon-orange color and carried above the foliage continuously through the summer in unusually large quantities, and with the plant having above average resistance to common garden diseases and with more winter-hardiness when compared to other varieties characteristic of the class.

No references cited.

ROBERT E. BAGWILL, Primary Examiner

UNITED STATES PATENT OFFICE

CERTIFICATE OF CORRECTION

Patent No. Plant 3,648 Dated November 12, 1974

Inventor(s) Gijsbert de Ruiter

It is certified that error appears in the above-identified patent and that said Letters Patent are hereby corrected as shown below:

In the heading to the printed specification, line 4, "The Conrad-Pyle Company" should read -- The Conard-Pyle Company --.

Signed and sealed this 18th day of February 1975.

(SEAL)
Attest:

RUTH C. MASON
Attesting Officer

C. MARSHALL DANN
Commissioner of Patents
and Trademarks